United States Patent
Cheng et al.

(10) Patent No.: US 11,674,157 B2
(45) Date of Patent: Jun. 13, 2023

(54) DONOR PLASMID VECTORS

(71) Applicant: Miami University, Oxford, OH (US)

(72) Inventors: Xiao-Wen Cheng, Oxford, OH (US); Hui Shang, Oxford, OH (US); Tyler Garretson, Oxford, OH (US)

(73) Assignee: Miami University, Oxford, OH (US)

( * ) Notice: Subject to any disclaimer, the term of this patent is extended or adjusted under 35 U.S.C. 154(b) by 111 days.

(21) Appl. No.: 16/012,686

(22) Filed: Jun. 19, 2018

(65) Prior Publication Data

US 2019/0002918 A1 Jan. 3, 2019

Related U.S. Application Data

(60) Provisional application No. 62/521,787, filed on Jun. 19, 2017.

(51) Int. Cl.
*C12N 15/86* (2006.01)
*C12N 15/866* (2006.01)

(52) U.S. Cl.
CPC ........... *C12N 15/866* (2013.01); *C12N 15/86* (2013.01); *C12N 2710/14121* (2013.01); *C12N 2710/14143* (2013.01)

(58) Field of Classification Search
CPC .............................. C12N 15/866; C12N 15/85
See application file for complete search history.

(56) References Cited

U.S. PATENT DOCUMENTS 7,498,166 B2 * 3/2009 Chambers .............. C12N 15/74
  435/235.1
2003/0228696 A1 * 12/2003 Robinson ................. C12N 7/00
  435/235.1

OTHER PUBLICATIONS

Carstens. Virologica Sinica 24(4):243-267, 2009 (Year: 2009).*

* cited by examiner

*Primary Examiner* — Marcia S Noble
(74) *Attorney, Agent, or Firm* — Calfee, Halter & Griswold, LLP

(57) ABSTRACT

Certain donor plasmid vectors such as pFastBac™1 and pFastBac™ Dual lack a cis DNA element upstream of the polh translation start codon (ATG) present in wild type (wt) *Autographa californica* multiple nucleopolyhedrovirus (AcMNPV), and contain a SV40 pA fragment. When a cis DNA element is inserted upstream of the 50 bp polh promoter and SV40 pA was replaced with a AcMNPV polh pA signal in pFastBac™1 and pFastBac™Dual, certain protein expression levels in High Five™ cells using the Bac-to-Bac® system reached that of the wt AcMNPV.

4 Claims, 6 Drawing Sheets
Specification includes a Sequence Listing.

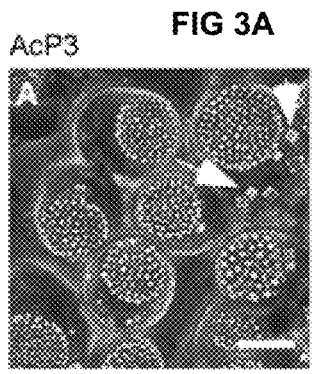
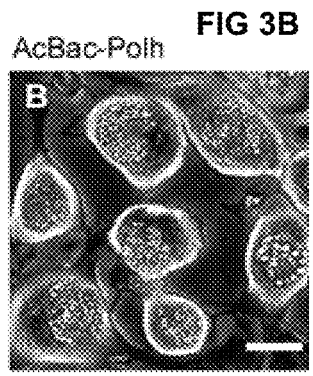
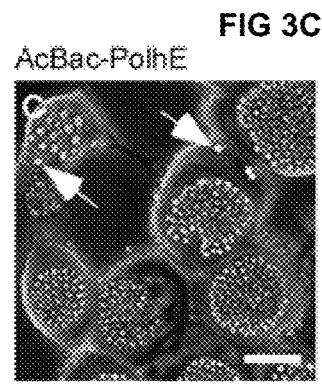
FIG 3A
FIG 3B
FIG 3C
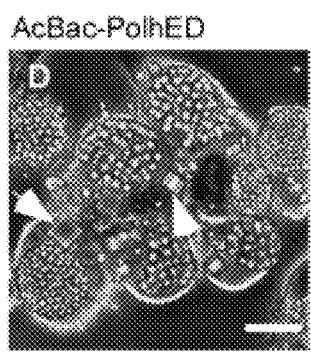
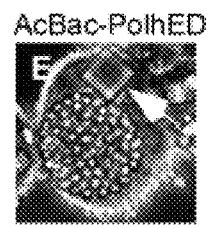
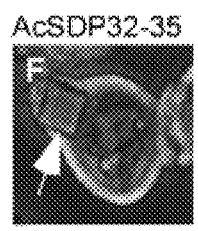
FIG 3D
FIG 3E
FIG 3F
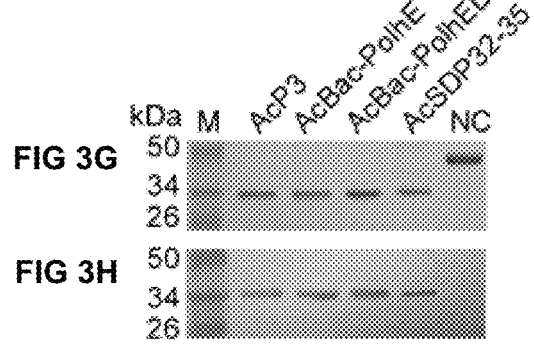
FIG 3G
FIG 3H
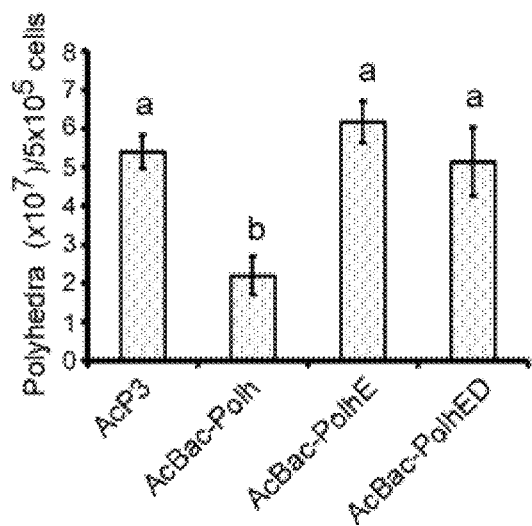
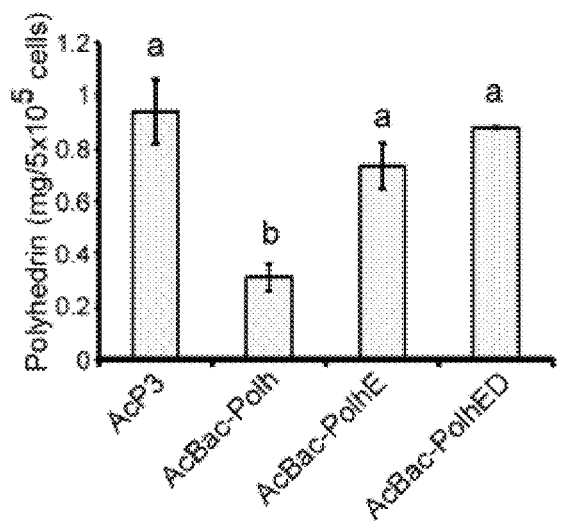
FIG 3I
FIG 3J

DONOR PLASMID VECTORS

RELATED APPLICATIONS

This non-provisional application claims the benefit of U.S. provisional application No. 62/521,787, filed Jun. 19, 2017, the content of which is hereby incorporated by reference herein as if recited in its entirety.

FIELD

The present invention relates generally to gene expression, and more particularly, to donor vectors.

BACKGROUND

Eukaryotic gene expression in the cells of other organisms is a well-known and useful tool for elucidation of gene function, determination of protein structure, and production of vaccines, among other uses. One widely used system for the expression of eukaryotic genes is the *Autographa californica* multiple nucleopolyhedrovirus (AcMNPV)-based Bac-to-Bac® expression system. This system includes a bacmid and five donor plasmid vectors (pFastBac™) and has been widely used for eukaryotic gene expression in insect cells to elucidate gene function and protein structure in research laboratories and biotechnology industries.

It has been reported that bacmids transposed with the pFastBac™ vectors expressed certain proteins in lower amounts than wild type (wt) AcMNPV in High Five™ insect cells.

SUMMARY

Purification and isolation of expressed proteins from infected organisms and cells can be costly and time consuming. Thus, improved protein yields are generally desirable. The general inventive concepts relate to a donor plasmid vector that demonstrates enhanced protein expression. Such enhanced protein expression can lead to faster results, reduced production costs, or both. The general inventive concepts are based, at least in part on the discovery that when a cis DNA element was inserted upstream of the 50 bp polh promoter and the SV40 pA was replaced with an AcMNPV polh pA signal in pFastBac™1 and pFastBac™Dual, certain protein expression levels equaled that of the wt AcMNPV in High Five cells using the Bac-to-Bac® system.

Applicants have found that the pFastBac™ vectors contain a 50 bp AcMNPV polyhedrin (polh) promoter and a SV40 polyadenylation (pA) signal for cloning genes of interest into the bacmid for expression. It has surprisingly been discovered that bacmids transposed with the pFastBac™ vectors expressed certain proteins at a reduced level (about 3-4 fold less) when compared to the wild type (wt) AcMNPV in High Five™ (HF) insect cells. An 80 bp cis element is 147 bp upstream of the 50 bp polh promoter, and a 134 bp polh pA signal are required in pFastBac™ vectors for cloning of genes into the bacmid to achieve the protein expression levels similar to that of the wt AcMNPV in HF cells. Attached to this document is Appendix A, a manuscript authored by the Applicants, which provides further context and details regarding the general inventive concepts. The content of Appendix A is hereby incorporated by reference as if recited in its entirety herein.

In certain embodiments, the general inventive concepts relate to an improved vector for gene expression. In certain embodiments, the general inventive concepts relate to a method for improving gene expression in a non-human cell. The method may comprise at least one of adding a cis element is 147 bp upstream of the 50 bp polh promoter and replacing SV40 pA with a AcMNPV polh pA signal. In certain embodiments, the inventive concepts contemplate a modified vector comprising at least one of a cis element and a polh pA signal.

In certain embodiments, the general inventive concepts relate to a bacmid transposed with an improved vector. In certain embodiments, the vector comprises a cis element. In certain embodiments, the vector comprises SEQ ID NO: 1. In certain embodiments, the cis element is 147 bp upstream of the 50 bp polh promoter. In certain embodiments, the general inventive concepts relate to a pFastBac™ type vector that comprises a polh pA signal. In certain exemplary embodiments, the polh pA signal comprises SEQ ID NO:2.

In certain embodiments, the general inventive concepts contemplate a method of improving protein expression in a cell comprising adding a cis element 147 bp upstream of a 50 bp polh promoter. In certain embodiments, the vector comprises SEQ ID NO:1.

In certain embodiments, the general inventive concepts contemplate a method of improving protein expression in a cell comprising replacing SV40 pA with a AcMNPV polh pA signal. In certain exemplary embodiments, the polh pA signal comprises SEQ ID NO:2.

The foregoing and other objects, features, and advantages of the general inventive concepts will appear more fully hereinafter from a consideration of the detailed description that follows. It is to be expressly understood, however, that the drawings are for illustrative purposes and are not to be construed as defining the limits of the invention.

BRIEF DESCRIPTION OF THE DRAWINGS

Various exemplary advantages of this invention will be apparent upon consideration of the following detailed disclosure of the invention, especially when taken in conjunction with the accompanying drawings wherein.

FIG. 3A, FIG. 3B, FIG. 3C, and FIG. 3D show phase contrast microscopy of polyhedra in HF cells infected with wt AcMNPV (AcP3), AcBac-Polh derived from pFastBac1, AcBac-PolhE containing an extend polh gene fragment in AcMNPV-based bacmid and AcBac-PolhED with vector polh promoter detected, respectively. Arrows point to cytoplasmic crystal formation. FIG. 3E and FIG. 3F, comparison of cytoplasmic crystals (an enlargement of a cell in D) in HF cells infected with AcBac-PolhED and AcSDP32-35 with a mutated nuclear localization signal in the polh gene. FIG. 3G and FIG. 3H show identification of cytoplasmic crystals by SDS-PAGE and western blot with an anti-polyhedrin antibody, respectively. NC, negative control. FIG. 3I and FIG. 3J show quantitative comparison of the production of polyhedra (I) and polyhedrin protein (J) in HF cells infected with different viruses that contain polh expressed as means±standard error of the mean. Means were calculated from three independent cell infections. The means with the same numbers of asterisks had no significant difference at p=0.05.

DETAILED DESCRIPTION

Figure 1A:
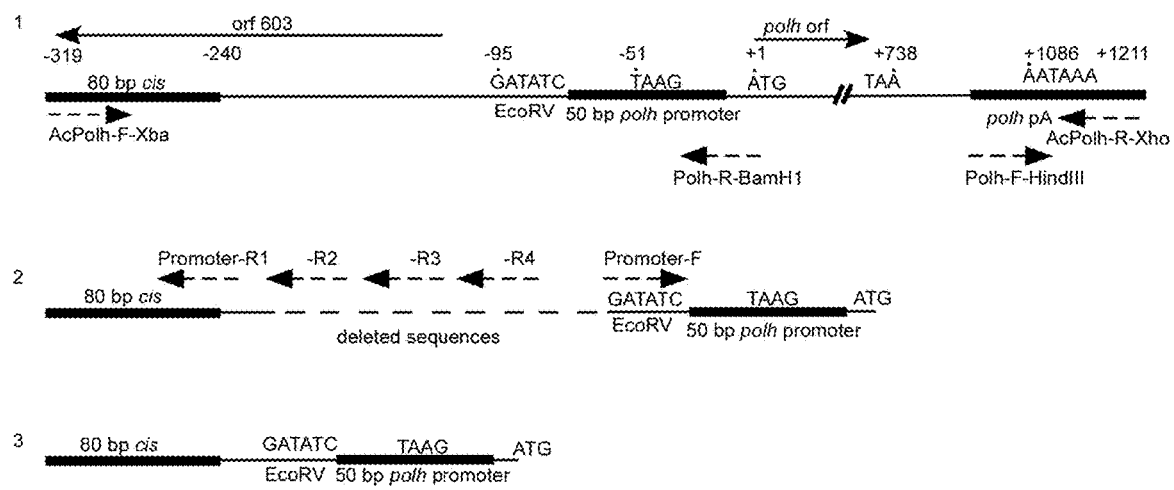
FIG. 1A, shows the polh locus and flanking regions. Schematic of the polh gene and the flanking regions containing the cis element, the 50 bp AcMNPV polh promoter and the polh polyadenylation signal (polh pA). Deletion of the upstream sequences of the 50 bp AcMNPV polh promoter in inverse PCR. Fusion of the cis element with the 50 bp AcMNPV polh promoter.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including published or corresponding U.S. or foreign patent applications, issued U.S. or foreign patents, and any other references, are each incorporated by reference in their entireties, including all data, tables, figures, and text presented in the cited references.

The terminology as set forth herein is for description of the exemplary embodiments only and should not be construed as limiting the disclosure as a whole. All references to singular characteristics or limitations of the present disclosure shall include the corresponding plural characteristic or limitation, and vice versa, unless otherwise specified or clearly implied to the contrary by the context in which the reference is made. Unless otherwise specified, "a," "an," "the," and "at least one" are used interchangeably. Furthermore, as used in the description and the appended claims, the singular forms "a," "an," and "the" are inclusive of their plural forms, unless the context clearly indicates otherwise.

To the extent that the term "includes" or "including" is used in the description or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both."

"Homology" or "sequence identity" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs which are known in the art. Any deviations appearing in the comparison between a given sequence and the above-described sequences of the invention may be caused for instance by addition, deletion, substitution, insertion or recombination.

Any combination of method or process steps as used herein may be performed in any order, unless otherwise specified or clearly implied to the contrary by the context in which the referenced combination is made.

The compositions described herein may comprise, consist of, or consist essentially of the essential elements of the products and methods as described herein, as well as any additional or optional element described herein or otherwise useful in binder applications or related applications.

Applicants have surprisingly found that measured protein expression levels using the Bac-to-Bac® system are not as high as the wild type (wt) AcMNPV in certain insect cell lines. The donor plasmid vectors such as pFastBac™1 and pFastBac™ Dual lack an cis DNA element and contain a 127 bp SV40 polyadenylation (pA) signal. The general inventive concepts are based, at least in part on the discovery that when the cis DNA element was inserted upstream of the 50 bp polh promoter and the SV40 pA was replaced with an AcMNPV polh pA signal in pFastBac™1 and pFastBac™Dual, certain protein expression levels equaled that of the wt AcMNPV in HF cells using the Bac-to-Bac® system.

In certain embodiments, the cis element comprises the following sequence: 5' actagagcatagtacgcagcttcttctagttcaattacaccattttttagcagcaccggattaacataactttccaaaatgttgtacgaaccgttaaaca 3' (SEQ ID NO: 1). In certain instances, SEQ ID NO: 1 is referred to as an 80 bp cis element and a cis element. Those of ordinary skill will understand that certain other functionality may be appended to a sequence to provide proper functionality (e.g., addition of a restriction site for cloning). The general inventive concepts also contemplate a sequence that is 85%, 86%, 87%, 88%, 89%, 90%, 91%, 92%, 93%, 94%, 95%, 96%, 97%, 98% or 99% identical to SEQ ID NO: 1.

In certain embodiments, the AcMNPV polh pA signal comprises the following sequence: 5' aaggttcgacgtcgttcaaaatattatgcgcttttgtatttctttcatcactgtcgttagtgtaca ttgactcgacgtaaacacgttaaataaagctaggacatatttaacatcgggcgtgttactcgactag 3' (SEQ ID NO:2). The general inventive concepts also contemplate a sequence that is 85%, 86%, 87%, 88%, 89%, 90%, 91%, 92%, 93%, 94%, 95%, 96%, 97%, 98% or 99% identical to SEQ ID NO:2.

The computer readable sequence listing entitled US20190002918_SR25.txt, created on Jun. 22, 2021, which is 4 KB in size, is hereby incorporated by reference herein.

Insect-specific baculoviruses in the family Baculoviridae have circular, double-stranded, DNA genomes in the range of 88-180 kb. Baculovirus research focuses on molecular and genetic studies, protein display as well as eukaryotic gene expression. Of all the baculoviruses, *Autographa californica* multiple nucleopolyhedrovirus (AcMNPV) is the most studied, and it is the foundation of the baculovirus expression vector system (BEVS). AcMNPV is preferred because it has the propensity to replicate efficiently in IPLB-Sf21-AE (Sf21), Sf9 (cloned from Sf21) and BTI-Tn-5B1-4 (High Five™) insect cells and can produce a high concentration or titer of budded virus (BV).

AcMNPV cell infection is accompanied by high levels of expression of a virus-encoded protein called polyhedrin, which forms large para-crystalline particles of 0.5-15 m in diameter in the nuclei during late phase infection. Production of these particles, formally known as polyhedra, requires large amounts of polyhedrin protein. This high level of protein is generated from a huge pool of mRNA produced under a very strong polyhedrin (polh) promoter. High-level polh promoter-mediated transcription requires 19 late expression factors (lef), one very late expression factor-1 (VLF-1), and a multifunctional protein (FP25K). Due to the high protein expression level mediated by the polh promoter in insect cells, AcMNPV has been used commercially to produce prophylactic vaccines, such as Cervarix® to fight against cervical cancer caused by human papillomavirus (HPV) and FluBlok□to reduce influenza virus infection in humans.

The most widely used AcMNPV polh promoter-based BEVS in the biotech industry and research laboratories is the Bac-to-Bac system, constructed in the late 1990's and marketed by Invitrogen. The Bac-to-Bac system involves site-specific transposition between a clonal copy of the AcMNPV genome (bacmid) and a pFastBac™ donor plasmid to produce recombinant bacmid DNA in DH10Bac™ *Escherichia coli* cells with the aid of a helper plasmid. The helper plasmid expresses a transposase to transfer the gene of interest from the pFastBac™ donor plasmid to a specific site within the bacmid in vivo. The Bac-to-Bac system eliminates the lengthy (up to 6 months) plaque-purification step required by the conventional homologous recombination method to produce the recombinant virus. Due to the ease with which foreign genes can be cloned into the AcMNPV bacmid, the Bac-to-Bac™ system along with its five pFastBac vectors (pFastBac1, pFastBac Dual, and pFastBacHT-a, -b, -c) have become a powerhouse second only to the *E. coli* expression system for eukaryotic protein structure studies, as shown in the worldwide Protein Data Bank.

All these donor plasmid vectors such as pFastBac™1, pDEST™20 and BaculoDirect™ vectors as well as pACE-Bac1 contain a 50 bp AcMNPV polh promoter embedded in a DNA fragment ranging from 88 to 129 bp depending on the vector for the projected high transcription activities and a SV40 polyadenylation (pA) signal for efficient mRNA 3' end processing and polyadenylation. It is likely that the designs of these donor plasmid vectors with these features are sought for the high level expression of eukaryotic proteins in insect cells.

Although baculoviruses are originally recognized as useful biological agents for agricultural and forest insect pest control, their popularity in biological research and use in the pharmaceutical industry is due to high yield expression of eukaryotic proteins in insect cells. In addition, more recent uses of baculovirus have been expanded into gene therapy to treat human diseases such as prostate cancer due to its safety of incapability to replicate in human cells. Amongst all the baculovirus expression vector systems developed since 1980's, the Bac-to-Bac® system is a milestone in biotechnology for eukaryotic protein expression since the system overcame a major drawback of the conventional BEVS that requires several rounds of plaque assay to obtain the purified recombinant viruses for protein expression in insect cells, which may take up to six months. Instead, the Bac-to-Bac® system uses the bacteria to produce separated colonies on agar plates to isolate and purify bacmid DNA for cell transfection and infection for protein expression in 7-10 days. However, donor plasmid vectors with the polh promoter are needed for cloning the gene of interest into the bacmid in *E. coli* cells.

Cloning of a polh fragment into pFastBac™1 produced similar polyhedrin protein expression levels to the wt AcMNPV.

Figure 2:
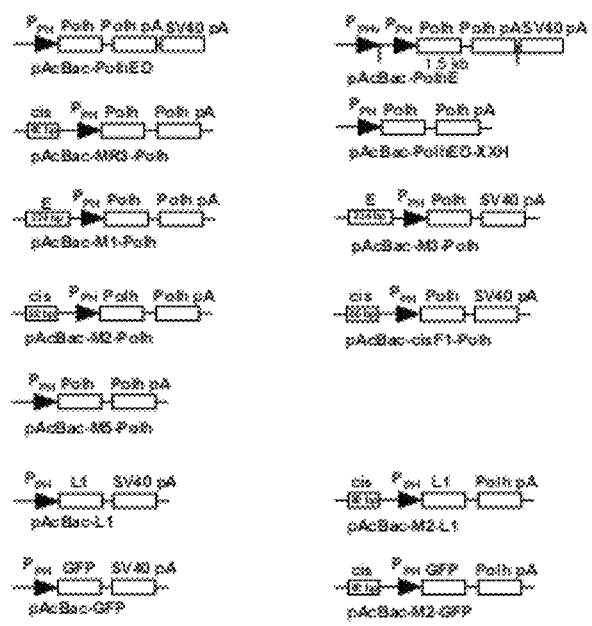
FIG. 2 shows a list of transfer donor vectors that were used for the production of the viruses. PPH, polyhedrin gene promoter. PPHv, polyhedrin gene promoter of the vector. Polh, polyhedrin gene. Polh pA, polyhedrin gene polyadenylation signal sequence. SV40 pA, SV40 polyadenylation signal sequence. E, extended sequences. Cis, cis element. L1, HPV16 L1 major capsid protein gene. GFP, green fluorescent protein gene.

To understand why protein expression levels of the Bac-to-Bac® system are lower than in wt AcMNPV (AcP3), a 1.5 kb polh fragment was cloned into pFastBac™1 (Invitrogen) to produce pAcBac-PolhE for bacmid virus, AcBac-PolhE generation (FIG. 2). This 1.5 kb polh fragment included the polh open reading frame (ORF) in addition to 319 bp (ntd+1 to −319) upstream and 473 bp (ntd+738 to +1,211) downstream sequences (FIG. 1A). At the same time, a DNA fragment containing only the polh ORF was cloned into pFastBac™1 to produce pAcBac-Polh for the generation of a bacmid virus, AcBac-Polh (FIG. 1A; FIG. 2). Infection of HF cells with AcP3, AcBac-PolhE, and AcBac-Polh resulted in no apparent difference between the production of polyhedra in AcP3 and AcBac-PolhE infected samples, while AcBac-Polh infection had clearly reduced levels of polyhedra (FIG. 3A, B, C).

Table 1 is a list of primers discussed herein.

TABLE 1

| Primer names | Primer sequences (restriction enzyme sites underlined) |
|---|---|
| AcPolh-F-XbaI (SEQ ID NO: 3) | 5'-tctagagcatagtacgcagcttcttc-3' |
| AcPolh-R-XhoI (SEQ ID NO: 4) | 5'-ctcgagtaacacgcccgatgttaaa-3' |
| AcPolh-F-EcoRI (SEQ ID NO: 5) | 5'-gaattcatgccggattattcatacc-3' |
| Hind-F (SEQ ID NO: 6) | 5'-ataaagctaggacatatttaacatcgggcgtgttag-3' |
| Hind-R (SEQ ID NO: 7) | 5'-atgtcctagctttatttaacgtgtttacgtcgagtc-3' |

TABLE 1 -continued

| Primer names | Primer sequences (restriction enzyme sites underlined) |
|---|---|
| Polh-F1-HindIII (SEQ ID NO: 8) | 5'-ccc<u>aagctt</u>cttgtagcagcaatctag-3' |
| Polh-R-BamH1 (SEQ ID NO: 9) | 5'-cgg<u>atccaa</u>tatttataggttttttattaca aaactg-3' |
| Promoter-R1 (SEQ ID NO: 10) | 5'- gttaatccggtgctgc-3' |
| Promoter-R2 (SEQ ID NO: 11) | 5'-aaaagggaggtgaactg-3' |
| Promoter-R3 (SEQ ID NO: 12) | 5'- gtctcattacaatggctg-3' |
| Promoter-R4 (SEQ ID NO: 13) | 5'-ctatatattgatagacatttccag-5' |
| promoter-F (SEQ ID NO: 14) | 5'-gatatcatggagataattaaaatg-3' |
| CisF1 (SEQ ID NO: 15) | 5'-gtagcatagtacgcagcttctt-3' |
| Polh-R-BamH1 (SEQ ID NO: 16) | 5'-cccggatccaatatttataggttttttttatta caaaactg-3' |
| Ac-Polh-F-EcoRI (SEQ ID NO: 17) | 5'-<u>gaattc</u>atgccggattattcatacc-3' |
| Ac-Polh-R-XbaI (SEQ ID NO: 18) | 5'-<u>tctaga</u>ttaatacgccggaccag-3 |
| HPV16 L1-F1-XbaI (SEQ ID NO: 19) | 5'-<u>tctaga</u>atggaggtgactttfatttacat c-3' |
| HPV16 L1-R1-HindIII (SEQ ID NO: 20) | 5'-<u>aagctt</u>ttacagcttacgttttttgcg-3' |

In addition, some HF cells infected with AcP3 and AcBac-PolhE generated cube-shaped cytoplasmic particles in the size range of 2-12 μm in diameter (FIG. 3A, C). These particles appeared indistinguishable from the cytoplasmic polyhedra formed by polyhedrin lacking the nuclear localization signal (NLS), which are produced by AcSDP32-35 infection in HF cells (FIG. 3A, C, E, F). Unlike what was observed in the AcBac-PolhE cell infection, HF cells infected with AcBac-Polh did not produce these cytoplasmic particles (FIG. 3B). When the particles from AcP3, AcBacPolhE, and AcSDP32-35 infected HF cells were purified by filtration and analyzed by SDS-PAGE, they all showed similar mobility, suggesting they may be composed of the polyhedrin protein (FIG. 3G). These large cytoplasmic particles were specifically recognized by an anti-polyhedrin antibody in a western blot analysis, and thus confirmed to be composed of polyhedrin (FIG. 3H). Sf21 and Sf9 cells infected with either AcP3 or AcBac-PolhE did not produce these cytoplasmic polyhedra (data not shown), suggesting that HF cells could support higher polyhedrin expression than either Sf21 or Sf9 cells. Phenotypic variation among the polyhedra produced during HF infection with the different viral constructs was informative but not quantifiable.

To provide quantitative insight, the levels of polyhedra produced during infection with the different virus constructs were determined. When HF cells were infected with AcP3, AcBac-PolhE, and AcBac-Polh, no differences in the number of polyhedra produced were detected between AcP3 and AcBac-PolhE; however, the number of AcBac-Polh polyhedra recovered was about 3-fold less than in the other infections (FIG. 3I). Since polyhedra from the three virus infections were different in sizes (FIG. 3A, B, C), the polyhedra from each viral infection were solubilized and the polyhedrin protein yields were estimated by the Bradford method. As with the number of polyhedra, the polyhedrin protein yields were similar between AcP3 and AcBac-PolhE, and both had about 3-fold more than AcBac-Polh (FIG. 3I, J). Collectively, these data suggest that DNA sequences present in pFastBac-PolhE but missing from pFastBac™1 and from the polh ORF can provide higher polyhedrin production using the Bac-to-Bac® system in HF cells.

Deletion of the vector polh promoter from pFastBac-PolhE showed similar polyhedrin protein expression levels to wild type AcMNPV.

In the donor plasmid pFastBac-PolhE, there are two copies of the polh promoter, one from pFastBac™1 (vector polh promoter) and the other from the upstream region of the polh ORF in the DNA fragment that was inserted into the multiple cloning site (MCS) (FIG. 1A1, 2; FIG. 2). One hypothesis for similar polyhedra yields between AcP3 and AcBac-PolhE could be that more polh mRNA was transcribed from the two polh promoters in AcBac-PolhE, thus leading to more polyhedrin protein production. To test this hypothesis, the vector polh promoter was deleted from pAcBac-PolhE to generate another donor plasmid, pAcBac-PolhED, and subsequently the bacmid virus construct AcBac-PolhED (FIG. 2). Infection of HF cells with either AcBac-PolhED or AcBac-PolhE yielded similar polyhedrin protein levels with many polyhedra per cell (MP phenotype), as seen in FIG. 3C, D. The production of polyhedra by AcBac-PolhED was also comparable to that of AcP3; both AcBac-PolhED and AcP3 showed cytoplasmic polyhedra during infection (FIG. 3A, C, D, E). Taken together, these data confirm that additional sequences upstream of the 50 bp polh promoter of pFastBac™1 are needed to achieve higher polyhedrin expression levels using the Bac-to-Bac® system in HF cells.

Figure 1B:
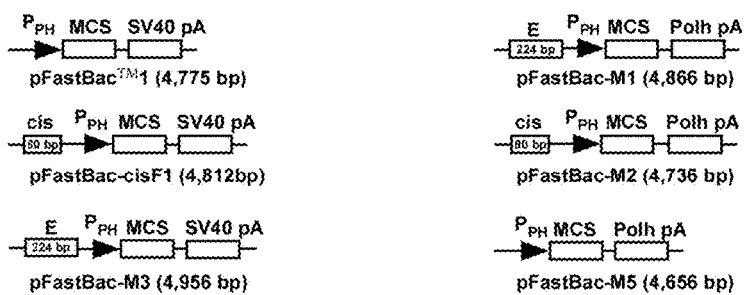
FIG. 1B shows a list of donor plasmid vectors derived from pFastBac1. pFastBac1 is the commercial vector that served as the source for construction of the different donor plasmid vectors developed in this study. E, extended sequences. Cis, cis element.
Figure 4A:
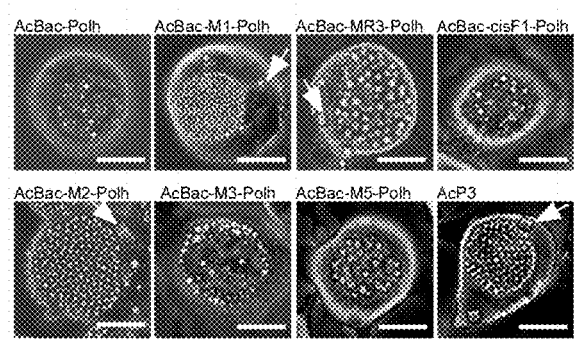
FIG. 4A shows Phase contrast microscopy of HF cells infected with different viruses derived from vectors presented in FIG. 1B, AcBac-MR3-Polh is an intermediate vector for AcBac-cisF1-Polh production (not shown in FIG. 1B). Both AcBac-MR3-Polh and AcBac-cisF1-Polh have the cis element, but AcBac-MR3-Polh has polh pA whereas AcBac-cisF1-Polh has SV40 pA.
Figure 4B:
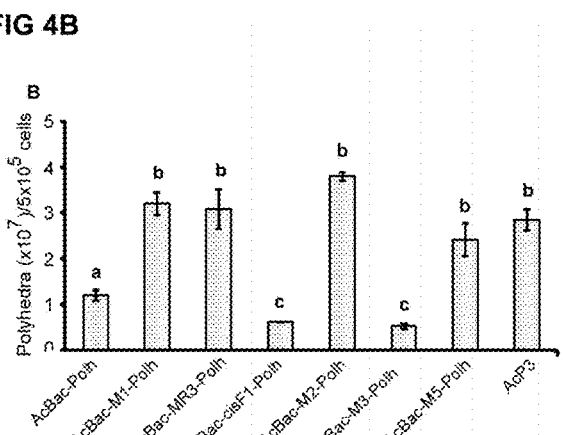
FIG. 4B shows a quantitative comparison of the production of polyhedra in HF cells infected with different viruses.

Since AcBac-PolhED, which has the extended polh promoter upstream sequences and polh pA, produced similar polyhedrin protein levels to AcP3 (FIG. 3I, J), we constructed our first improved donor plasmid vector by using inverse PCR to generate pFastBac-M1 (FIG. 1B). This donor vector has a DNA fragment with the extended upstream sequences (E), the 50 bp polh promoter, an MCS, and a polh pA fragment (FIG. 1B). We then cloned the polh ORF into pFastBac-M1 and generated the AcBac-M1-Polh virus (FIG. 2). Infection of HF cells with AcBac-M1-Polh resulted in the same MP phenotype seen with AcP3, along with the production of cytoplasmic polyhedra (FIG. 4A). Comparison of polyhedra yields between HF cells infected with either AcBac-M1-Polh or AcP3 showed no difference, and both generated about 3-fold more polyhedra than AcBac-Polh (FIG. 4B). However, the DNA elements in pFastBac-M1 responsible for elevated polyhedra production in HF cells remained unknown.

A cis element upstream of the polh promoter elevated protein expression yields. In certain embodiments, the cis element comprises the following sequence: 5' actagagcatagtacgcagatatctagttcaattacaccatttttagcagcaccggattaacataacttccaaaatgttgt acgaaccgttaaaca 3' (SEQ ID NO 2).

To understand why AcBac-PolhED and AcBac-M1-Polh were able to produce more polyhedrin than AcBac-Polh, inverse PCR was used in an attempt to map the 227 bp region upstream of the EcoRV site of the polh promoter in pFastBac-PolhED (FIG. 1A2, Table 1). Inverse PCR with the promoter-F forward primer paired with promoter-R1, -R2 or -R4 reverse primers did not yield any useful clones. However, inverse PCR using the promoter-F/promoter-R3 primer pair produced an unexpected 144 bp deletion in the middle of the 227 bp polh upstream region, thus producing donor plasmid vector pAcBac-MR3-Polh (FIG. 2), This vector, containing a cis element upstream of the 50 bp polh promoter, the polh ORF, and polh pA sequences, was used to generate the bacmid virus AcBac-MR3-Polh via the Bac-to-Bac® system. Infection of HF cells with AcBac-MR3-Polh showed MP and cytoplasmic polyhedra similar to those of AcP3, AcBac-PolhED and AcBac-M1-Polh (FIG. 3D; FIG. 4A).

SV40 pA in pFastBac™1 contributed to lower protein expression levels.

Since the cis element of AcBac-MR3-Polh was able to improve the polh promoter-mediated polyhedrin protein expression levels to match AcP3, AcBac-PolhED and AcBac-M1-Polh (FIG. 3; FIG. 4A, B), we wanted to investigate whether insertion of this cis element upstream of the polh promoter of pFastBac™ 1 could enhance polh expression. To test this hypothesis, the 50 bp polh promoter of pFastBac™1 was replaced with the DNA fragment containing the cis element and 50 bp polh promoter from pFastBac-MR3-Polh, but the SV40 pA fragment was retained, to generate donor plasmid vector pFastBac-cisF1 (FIG. 1A2). The polh ORF was cloned into pFastBac-cisF1 to generate pAcBac-cisF1-Polh for the production of the bacmid virus AcBac-cisF1-Polh. Infection of HF cells with AcBac-cisF1-Polh showed lower polyhedra production compared to that of AcBac-MR3-Polh (FIG. 4A, B). These data suggest that the SV40 pA signal reduced the production of polyhedra.

To confirm this observation, the polh ORF was cloned into pFastBac-M3, which contained the 227 bp sequences upstream of the polh promoter but had the SV40 pA signal, and ultimately the bacmid virus AcBac-M3-Polh was generated (FIG. 2). Infection of HF cells with AcBac-M3-Polh resulted in polyhedra production lower than AcBac-M1-Polh (FIG. 4A, B). Thus, both donor plasmid vectors confirmed that the SV40 pA signal reduces polyhedra production. These data also suggest that in order to improve expression levels, this SV40 pA signal should be replaced with an AcMNPV viral pA, or more specifically the polh pA, since AcBac-M1-Polh contained the polh pA signal.

Polyhedrin pA plays a role in donor plasmid vectors for higher protein expression.

To test if polh pA could help donor plasmid vectors such as pFastBac™1, pFastBac-cisF1 and pFastBac-M3 produce more polyhedrin protein, the SV40 pA sequence in pFast-Bac™1 and pFastBac-cisF1 was replaced by polh pA to generate pFastBac-M5 and pFastBac-M2, respectively (FIG. 1B). Subsequently, the polh ORF was cloned into pFastBac-M2 and pFastBac-M5 to generate pAcBac-M2-Polh and pAcBac-M5-Polh for the production of the bacmids AcBac-M2-Polh and AcBac-M5-Polh (FIG. 2). Infection of HF cells with either AcBac-M2-Polh or AcBac-M5-Polh yielded levels of polyhedra similar to AcBac-M1-Polh and AcP3, which were all higher than AcBac-Polh, AcBac-cisF1-Polh and AcBac-M3-Polh (FIG. 4A, B). However, AcBac-M2-Polh resulted in the highest level of polyhedra production among the viruses containing the polh pA signal (FIG. 4A, B).

Figure 4C:
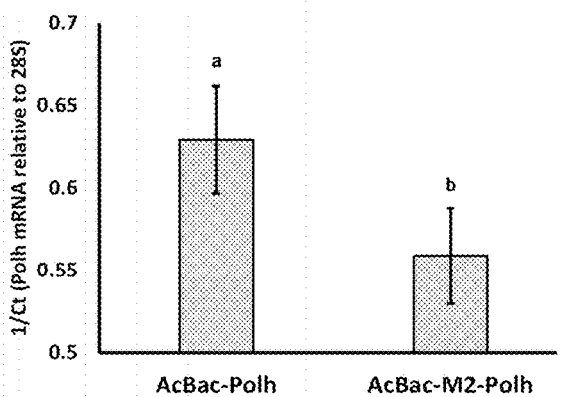
FIG. 4C shows comparison of polh mRNA levels between AcBac-Polh and AcBac-M2-Polh in HF cells. High Five cells were infected with AcBac-Polh and AcBac-M2-Polh. Total RNA were isolated from infected cells for transcription level comparison of polh mRNA by real-time qPCR. Ct, threshold cycle.
Figure 4D:
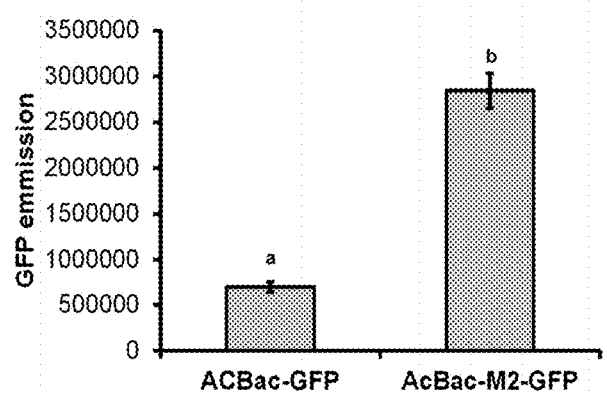
FIG. 4D shows comparison of GFP expression between AcBacGFP and AcBac-M2-GFP in HF cells. All experiments were conducted in triplicates. Error bar, the standard error of the mean. Means with the same letter had no significant difference at p=0.05.
Figure 5A:
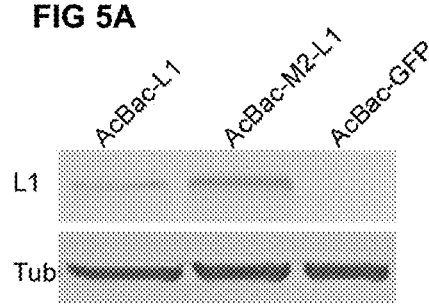
FIG. 5A shows Western blotting analysis of L1 protein expression levels in HF cells infected with AcBac-L1 derived from pFastBac1 or AcBac-M2-L1 derived from pFastBac-M2. AcBacGFP was used as a negative control.
Figure 5B:
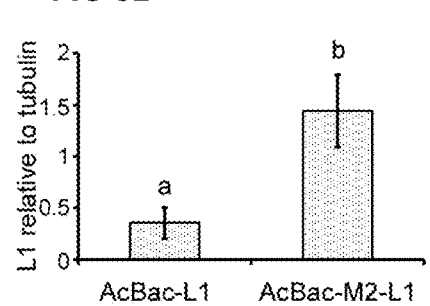
FIG. 5B shows quantitative comparison of L1 expression. At day 3, P.I. infected cells were harvested for L1 expression analysis. Equal amounts of protein (100 µg) were loaded to each lane in SDS-PAGE. Western blotting signals for A in triplicate were quantified by densitometry. Error bars, the standard error of the mean. Means with the same letter had no significant difference at p=0.05.

To support the polh expression data that indicated pFast-Bac-M2 is the best donor vector developed in this study for higher protein expression, the HPV16 L1 genes were cloned into the commercial pFastBac™1 and improved pFastBac-M2 vectors to generate pAcBac-L1 and pAcBac-M2-L1 for the production of AcBac-L1 and AcBac-M2-L1 bacmid viruses, respectively (FIG. 2). Similar to the higher expression level of AcBac-M2-Polh relative to AcBac-Polh, HF cells infected with AcBac-M2-L1 also showed about 4-fold more L1 expression than AcBac-L1 (FIG. 4A, B; FIG. 5A, B). Furthermore, the GFP expression level of AcBac-M2-GFP showed 3-fold higher than AcBacGFP in HF cells (FIG. 4D).

Since all the pFastBac-M2-derived viruses (AcBac-M2-Polh, AcBac-M2-L1 and AcBac-2 M2-GFP) showed 3-4 fold more protein production than the viruses derived from the standard commercial vector pFactBac1 (AcBac-Polh, AcBac-L1 and AcBacGFP) in HF cells (FIG. 4A, B, D, FIG. 5A, B), we wondered if this observation was correlated with the mRNA levels. When polh mRNA levels of AcBac-Polh and AcBac-M2-Polh were compared by real-time qPCR, polh mRNA from AcBac-Polh showered about 1-fold higher than that from AcBac-M2-Polh in HF cells (FIG. 4C).

Figure 1C:
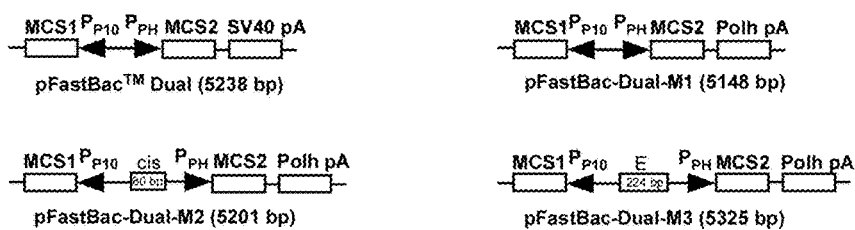
FIG. 1C shows a comparison of commercial dual vector pFastBac-Dual with improved dual expression vectors.
Figure 6A:
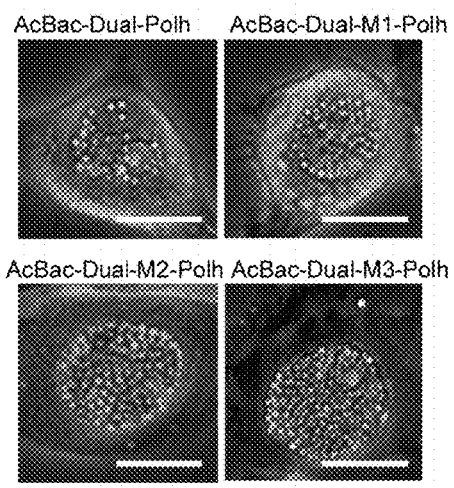
FIG. 6A shows phase contrast microscopy of HF cells infected with different viruses derived from the dual vectors expressing AcMNPV polh. Scale bar=10 m.
Figure 6B:
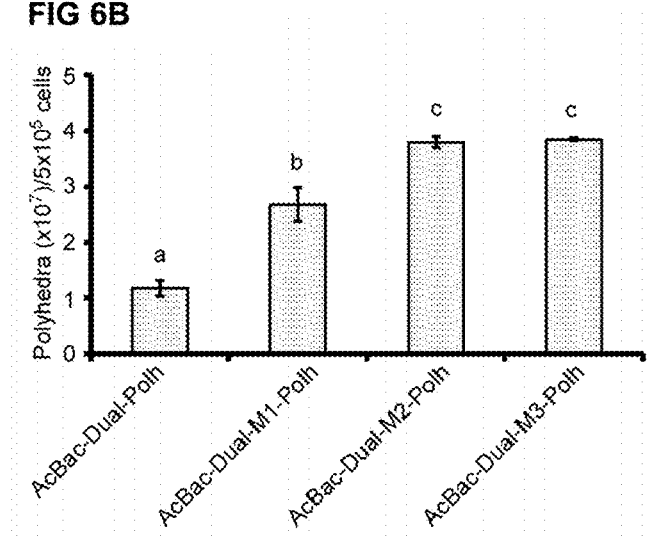
FIG. 6B shows quantitative comparison of the production of polyhedra in HF cells infected with different viruses. The figures show improved pFastBac-Dual vectors and comparison of the production of polyhedra in HF cells infected with bacmids derived from the various dual vectors. HF cells were infected separately with different viruses in triplicate. At day 3 P.I. data were collected from infected cells. Polyhedra were extracted from infected cells for enumeration. Means with the same letter had no significant difference at p=0.05.

Improved pFastBac™1-based donor plasmid vectors such as pFastBac-M1 and pFastBac-M2 all have the cis element and polh pA in addition to the 50 bp polh promoter (FIG. 1B). Whether these elements were also required in the pFastBac™ Dual vector for improved protein expression in HF cells remained unknown. To test the effect of these elements, the polh ORF was inserted into the commercial pFastBac™ Dual and the newly generated pFastBac-Dual-M1, pFastBac-Dual-M2 and pFastBac-Dual-M3 vectors for bacmid production of AcBac-Dual-Polh, AcBac-Dual-M1-Polh, AcBac-Dual-M2-Polh and AcBac-Dual-M3-Polh, respectively (FIG. 1C). The levels of polyhedra produced from AcBac-Dual-Polh and AcBacBac-Dual-M1-Polh infections were lower than those from AcBacBac-Dual-M2-Polh and AcBacBac-Dual-M3-Polh (FIG. 6A, B). Moreover, AcBac-Dual-M1-Polh produced 2-fold more polyhedra than AcBac-Dual-Polh and AcBacBac-Dual-M2-Polh, and AcBacBac-Dual-M3-Polh yielded 3-fold more than AcBac-Dual-Polh (FIG. 6A, B). Since pFastBac-Dual-M2 and pFastBac-M2 are similar in that they both contain the cis element and polh pA, the improved polh expression using pFastBac-Dual-M2 supports the findings that these elements are required for high protein expression in pFastBac-M2. Similar polh expression levels between AcBac-Dual-M3-Polh and AcBac-Dual-M2-Polh further support the finding that the cis element and polh pA are the only additions to the donor plasmid vectors required to elevate 4 protein yields in the Bac-to-Bac® expression system (FIG. 6A, B).

Applicants have identified a cis element 147 bp upstream of the 50 bp polh promoter of AcMNPV and the polh pA that are required for the commercial pFastBac™ vectors to transpose certain genes into the bacmid to achieve expression levels to that of the wt AcMNPV in HF insect cells. This sequence was discovered when the first baculovirus genome was sequenced, but not yet characterized (Ayres et al., 1994). Therefore, this cis element and the polh pA can be used to modify many baculovirus expression vectors to improve protein expression levels in HF insect cells.

Among all the BEVSs developed since the 1980's, the emergence of the Bac-to-Bac® system represented a key milestone for biotechnology and eukaryotic protein expression because this system has overcome a major drawback of the conventional BEVSs, the requirement for several rounds of plaque assay to obtain a purified recombinant virus. Instead, the Bac-to-Bac® system uses *E. coli* for recombination, isolation of pure colonies, and extraction of bacmid DNA for cell transfection, to produce pure recombinant virus for protein expression in 7-10 days. However, donor plasmid vectors with the polh promoter are needed to recombine the gene of interest into the bacmid in *E. coli* cells.

The polh promoter used in the donor plasmid vectors is one of the strongest baculovirus promoters during insect cell infection. The 50 bp AcMNPV polh promoter was mapped by linker-scan mutations in the polh promoter region of the AcMNPV genome. Following this discovery, the 50 bp polh promoter has been inserted into multiple donor plasmid vectors, such as the popular pFastBac™1 plasmid vector studied in this project, to recombine the gene of interest into the bacmid. It is apparent why previous polh promoter mapping did not find this cis element, since the mapping was directed downstream toward the polh mRNA transcription start site TAAG, whereas the cis element is 147 bp upstream of the 50 bp polh promoter (FIG. 1A1, 2).

Initially applicants deemed this DNA element to be an enhancer, but later decided it is instead a cis element because there is another copy of the sequence in the non-essential ORF 603, which is separated from the polh promoter by a 3.2 kb DNA plasmid sequence in the recombinant bacmid. A previous study discovered a 2,555 bp AcMNPV sequence upstream of polh that includes ORF 603, lef2, ORF5 and ORF4, and that enhances the promoter activity of cytomegalovirus (CMV), heat shock 70 from *Drosophila*, and p35 of baculovirus. In addition, another study reported that over expression of IE1 and IE0 as well as a homologous repeated transcription enhancer sequence of AcMNPV enhances polh promoter activity. However, these elements are either much larger than the cis DNA sequence or the factors are different from what we discovered in this report. Furthermore, this cis element is different from another 293 bp enhancer-like element located 1 kb upstream of the ATG site of polh that was reportedly able to enhance the polh promoter activity of *Bombyx mori* NPV.

Although the cis element enhanced the polh promoter of pFastBac™1 to allow the bacmid to produce higher levels of protein, it is uncertain whether the entire sequence is needed for enhanced protein expression. In addition, adding this cis element alone did not allow The rationale for inserting SV40 pA into the early donor plasmid vectors was to facilitate transcription termination and mRNA polyadenylation, thereby improving mRNA stability for anticipated higher protein expression. It was observed that a gene expression cassette with SV40 pA expressed less reporter protein than one with the p10 3'UTR. Furthermore, it has been argued that additional pA signal sequences should not be added to baculovirus expression vectors. Our data in this report showed that AcBac-Polh that has SV40 pA displayed more polh mRNA levels than AcBac-M2-Polh that has polh pA (FIG. 4C). This result is supported by our early study that SV40 pA increases mRNA levels but reduces protein expression levels. It is unclear why the levels of polh expression regulated by the SV40 pA sequence and polh promoter were lower than with the polh pA (FIG. 4, 6). One may speculate that since SV40 pA is foreign to AcMNPV and HF cells, there might be small RNA, micro RNA or protein(s) from the virus or the host cells that interact with SV40 pA to negatively regulate protein synthesis.

Previously HF cells showed higher protein expression yields than Sf9 cells infected with recombinant AcMNPV. It is unknown why cytoplasmic polyhedra were produced in HF cells infected with AcP3, AcBac-PolhE, AcBac-PolhED, AcBac-M1-Polh and AcBac-M2-Polh but not in Sf21 and Sf9 cells, supporting the finding of higher protein expression in HF cells than in Sf9 cells (FIG. 3, 4). It is possible that the larger cell size of HF that is about twice the sizes of Sf9 and Sf21 enables HF cells to synthesize more proteins. It is also possible that polyhedrin crystallization in the cytoplasm reflects the higher level of cytoplasmic polyhedron (much higher than that needed for crystallization), allowing it to crystalize prior to transport to the nucleus.

Since the pFastBac-M2 and pFastBac-Dual-M2 vectors have the same MCS as commercial pFastBac™1 and pFastBac™ Dual, researchers who are using these vectors for protein expression can simply transfer their genes of interest into the improved pFastBac-M2 and pFastBac-Dual-M2 vectors to achieve higher protein expression yields and reduce protein production costs. All other baculovirus vectors using the 50 bp polh promoter and SV40 pA can also be modified to include the cis element and to replace SV40 pA with the polh pA fragment for improved protein expression yields in HF cells.

The rationale to insert SV40 pA to the donor plasmid vectors is to facilitate transcription termination and mRNA polyadenylation, thereby believed to improve mRNA stability for more protein expression. It was reported in an early publication that a gene expression cassette with SV40 pA expresses lower reporter proteins than that with a p10 3'UTR, suggesting that the p10 3' UTR is preferred over these expression cassettes with SV40 pA. In addition, it has also been argued that additional polyadenylation signal sequences should not be added to baculovirus expression vectors. In fact, Applicants found that SV40 pA could increase mRNA levels but protein expression levels were reduced. It is unknown why the levels of polh expression with the SV40 pA sequence under the regulation of the polh promoter were lower than that with the polh pA. One may speculate that since SV40 pA is foreign to AcMNPV and HF cells, there might be regulative small RNA, micro RNA or protein(s) from the virus or the host cells that negatively regulate protein synthesis.

For high protein expression using the Bac-to-Bac® system, the insect cells also play a significant role. It has been reported that HF cells could support higher secreted protein production than Sf21 and Sf9 cells using the BEVS. Our discoveries of accumulation of large cytoplasmic polyhedrin crystals in addition to nuclear production of polyhedra by AcP3, AcBac-PolhE, AcBac-PolhED AcBac-M1-Polh and AcBac-M2-Polh infections in HF cells support this early report (FIG. 2A, C, D, FIG. 4 A). It is unknown why some HF cells could produce these large cytoplasmic polyhedrin crystals. It is known that the nuclear localization signal of polyhedrin is required to traffic polyhedrin synthesized in the cytoplasm to the nucleus (FIG. 2F). One possible explanation could be that in some of the HF cells that support production of cytoplasmic polyhedra are cells with even higher protein expression than these without production of cytoplasmic polyhedra. In fact, clonal HF cells have been isolated showing higher protein expression than the parental HF cells. These HF cells showing production of cytoplasmic polyhedra might run out of importin thus polyhedrin starts crystallization in the cytoplasm due to over-expression of polyhedrin.

Having generally described this invention, a further understanding can be obtained by reference to certain specific examples illustrated below which are provided for purposes of illustration only and are not intended to be all inclusive or limiting unless otherwise specified.

EXAMPLES

Insect cell lines used in this project included HF, Sf21 and Sf9 cells were obtained from Invitrogen. The virus used in this study was AcP3, a plaque purified AcMNPV E2 strain originally received from Dr. Max Summers of Texas A&M University. Plasmids and bacterial strains included for this study were pFastBac™1, pFastBac™Dual and the host bacterial strain DH10Bac obtained in a kit, the Bac-to-Bac® system from Invitrogen.

Although the exact reason for the poorer protein expression yield of the Bac-to-Bac® system compared to the wt AcMNPV was unknown, we first amplified a 1.5 kb DNA fragment by PCR using a forward primer AcPolh-F-XbaI and reverse primer AcPolh-R-XhoI and cloned it into the pGEM-T Easy vector (Promega, Madison Wis.) to produce pGEM-PolhE (Table 1). This 1.5 kb fragment contained the polh ORF with 319 bp of DNA sequence upstream of the polh ORF start codon ATG. The 319 DNA sequence included the 50 bp polh promoter and additional upstream sequences. The 1.5 kb fragment also included the polh downstream untranslated region (UTR) containing a 472 bp polh polyadenylation signal (pA) between nucleotides (ntd) 739-1,211 (FIG. 1A1; FIG. 2).

To evaluate the effect of this 1.5 kb fragment on polyhedrin protein expression using the Bac-to-Bac® system, the 1.5 kb fragment from pGEM-PolhE was retrieved with restriction endonucleases (REN) XbaI and XhoI (NEB, Ipswich, Mass.) and inserted into these sites in pFastBac™1 to generate a clone (pAcBac-PolhE) (FIG. 1B; FIG. 2). Competent DH10Bac cells were transformed with pAcBac-PolhE and recombinant bacmid clones were screened and selected using X-gal and IPTG on antibiotic plates, following conditions recommended by Invitrogen. One confirmed recombinant bacmid with the 1.5 kb polh fragment was used to transfect HF cells to generate AcBac-PolhE budded virus (BV).

The AcBac-PolhE construct had two polh promoters; one from the parental pFastBac1 vector and one from the upstream sequences of the 1.5 kb DNA fragment (FIG. 2). Also, AcBac-8 PolhE had two pAs; the SV40 pA from the pFastBac1 vector and the polh pA from the 1.5 kb 9 DNA fragment (FIG. 2). To delineate the functionality of the 1.5 kb insert in AcBac-PolhE, the vector polh promoter and SV40 pA of pAcBac-PolhE were deleted. The vector polh promoter was deleted by digestion of pAcBac-PolhE with BstZ17I and XbaI, followed by Klenow enzyme treatment and self-ligation with T4 DNA ligase (NEB) to generate the plasmid pAcBac-PolhED. The SV40 pA was deleted by digestion of pAcBac-PolhED with XhoI and AvrII, followed by Klenow enzyme treatment and self-ligation with T4 DNA ligase to generate plasmid pAcBac-PolhED-XX. To use the unique HindIII site of the donor vector for cloning genes, the HindIII site in the UTR of polh was mutated from AAGCTT to AAGCTA by site-directed mutagenesis using the primer pair Hind-F and Hind-R (Table 1) and the QuikChange II Site-Directed Mutagenesis Kit (Agilent Technologies, Santa Clara, Calif.). This resulted in the generation of the plasmid pAcBac-PolhED-XXH (FIG. 2), which was necessary for the subsequent steps of engineering pFastBac1-M1.

Inverse PCR was used to produce pFastBac-M1. A pair of primers (Polh-F1-HindIII and Polh-R-BamH1) using pFastBac-PolhED-XXH DNA as a template and the high fidelity pfu enzyme (Agilent Technologies) to produce a linear DNA fragment that was digested with HindIII and BamHI. The digested product was ligated to the multiple cloning site fragment retrieved from pFastBac™1 digested with HindIII and BamH1 with T4 DNA ligase to produce pFastBac-M1.

To determine if all the upstream sequences of the polh promoter were required for the improved protein expression yield of pFastBac-M1, four reverse primers (Promoter-R1, -R2, -R3 and -R4, Table 1) were designed to map the 240 bp region upstream of the promoter (FIG. 1A2; Table 1). Each of the four reverse primers was paired with primer promoter-F in inverse PCR, in order to delete a defined length of DNA sequence in the 240 bp region immediately upstream of the polh promoter, using pAcBac-PolhED-XXH DNA as a template with the pfu DNA polymerase. The promoter-F and promoter-R3 reaction ultimately produced the clone pAcBac-MR3-Polh, which was missing 144 bp (ntd −240 to −96, FIG. 1A3) of the 240 bp upstream region but maintained the rest of the plasmid sequences, including a cis element upstream of the 50 bp polh promoter and the polh pA (FIG. 2). Competent DH10Bac™ cells were transformed with pAcBac-MR3-Polh DNA to generate AcBac-MR3-Polh. This bacmid DNA was transfected into HF cells to produce BV for infection of HF cells, which were used to compare polyhedra production with AcP3.

To generate pFastBac-cisF1, a pair of primers (CisF1 and Polh-R-BamH1) and pAcBac-MR3-Polh DNA as the template were used to amplify a 136 bp (ntd+2 to −319, FIG. 1A3) fragment that contained the cis element and the polh promoter, with the ATG sequence of the polh ORF mutated to ATT (in Polh-R-BamH1) (Table 1). This PCR product was agarose gel purified and cloned into the SnaBI and BamHI sites of pFastBac™1 to generate the pFastBac-cisF1 donor plasmid vector (FIG. 1B). Ultimately, this vector had an cis element upstream of the polh promoter and SV40 pA.

To generate pFastBac-M2, the cis element and polh promoter fragment were retrieved by digestion of pFastBac-cisF1 with SnaBI and BamHI. This fragment was then inserted into the SnaBI and BamHI sites of pFastBac-M1, thus producing pFastBac-M2 that contained the cis element upstream of the polh promoter and polh pA (FIG. 1B).

To generate pFastBac-M3, the extended polh upstream fragment (224 bp plus the polh promoter) from pFastBac-M1 was retrieved by digestion with SnaBI and BamHI and inserted between the SnaBI and BamHI sites of pFastBac™I, thus producing pFastBac-M3 with 224 bp extended sequence upstream of the polh promoter and SV40 pA (FIG. 1B).

To generate pFastBac-M5, pFastBac™1 and pFastBac-M1 were separately cleaved by double-digestion with BamHI and EcoRV and the digested DNA fragments were separated by agarose gel electrophoresis. The fragment containing the 50 bp polh promoter and Tn7R from pFastBac™I and the fragment containing the polh pA and Tn7L were gel-extracted and ligated by T4 DNA ligase for bacterial transformation to produce pFastBac-M5 (FIG. 1B).

To improve this dual vector, the AcMNPV polh pA sequence was first cloned into pFastBac Dual. This was achieved by a digestion of pFastBac-M2 and pFastBac Dual separately with HindIII and EcoRV. The DNA fragments were separated by agarose gel electrophoresis. The 3,374 bp HindIII/EcoRV fragment that contained the polh pA sequence and the 1,774 bp HindIII/EcoRV fragment that contained the MCS and the p10 promoter were gel purified and ligated for the production of pFastBac-Dual-M1 (FIG. 1C).

To insert the cis element into pFastBac-Dual-M1, the plasmid pFastBac-M2 was digested with SnaB I and Bam H1 and pFastBac-Dual-M1 was digested with BstZ17I and BamH I followed by agarose gel electrophoresis. The 201 bp fragment containing the cis element and the 50 bp polh promoter from the pFastBac-M2 digestion and the larger fragment from the pFastBac-Dual-M1 digestion were gel-purified and ligated for the production of pFastBac-Dual-M2 (FIG. 1C). To further confirm the significance of the cis element in enhancing the 50 bp polh promoter activity, the 224 bp polh upstream sequences in pFastBac-M1 were retrieved by a double-digestion of SnaBI and BamHI and ligated into the BstZ17I and BamHI by using T4 DNA ligase (NEB) to produce pFastBac-M3 (FIG. 1C).

HF cells at 5×10$^5$ cells per 35 mm dish were infected with AcP3, AcBac-PolhE, AcBac-PolhED or AcSDP33-35 at an MOI of 1. At day 3 post infection when cytoplasmic crystals appeared, the medium was removed and 1% SDS was added to lyse the cells. The lysates were filtered with a Whatman Nuclepore Track-Etch membrane (pore size 8 μm). Crystals maintained on the membrane were washed with TE buffer in a 1.5 microcentrifuge tube. An aliquot from each infection was examined under a microscope for purity of cytoplasmic particles. To determine the nature of these cytoplasmic particles, the purified particles were first solubilized by treatment of 0.1 M Na$_2$CO$_3$ (pH 10.5). The concentrations of the solubilized proteins were determined by using the Bradford protein assay kit (Bio-Rad) following the recommended procedures. About 50 ug of solubilized crystal proteins from each virus infection was analyzed on a 12% SDS-PAGE. A duplicate gel was used to transfer proteins to a Protran nitrocellulose membrane (Scheicher & Schuell, Keene, N.H.) for antibody detection. An anti-polyhedrin antibody of Choristoneurafumiferana MNPV was provided by Dr. Basil Arif of Great Lake Forestry Center, Canada was used at a 1:10,000 dilution in western blot analysis. Following the primary polyhedrin antibody binding, the blot was incubated with horseradish peroxidase (HRP)-linked anti-rabbit IgG at 1:1,000 (Cell Signaling, Danvers, Mass.). Antibody binding was visualized using HRP color development Reagent (Bio-Rad, Hercules, Calif.) in a western blot analysis.

For polyhedrin protein expression comparisons between different viral constructs, the ORF of AcMNPV polh was amplified using a pair of oligo primers (Ac-Polh-F-EcoRI and Ac-Pol-R-XbaI, Table 1) with Taq and cloned into pGEM-T Easy (Promega). After sequencing confirmation, the polh ORF was digested with EcoRI and XbaI to clone into commercial pFastBac™1 and the improved donor vectors in order to construct pAcBac1-Polh, pAcBac-M1-Polh, pAcBac-cisF1-Polh, pAcBac-M2-Polh, pAcBac-M3-Polh, and pAcBac-M5-Polh (FIG. 2). To generate viruses for polh expression comparison, competent DH10Bac cells were transformed with plasmid DNA from these constructed vectors to produce recombinant bacmids, following the procedures recommended by Invitrogen. HF cells were transfected with recombinant bacmids by the polyethylenimine (PEI) method to produce BVs of AcBac-Polh, AcBac-M1-Polh, AcBac-cisF1-Polh, AcBac-M2-Polh, AcBac-M3-Polh and AcBac-M5-Polh (Ogay et al., 22 2006). HF cells were infected with AcP3, AcBac-PolhE, AcBac-PolhED at an MOI of 1 in triplicate. At day 4 P.I., infected cells were photographed and the media were removed and replaced with 1 ml of 1% SDS to lyse the cells and release polyhedra by rocking for 30 min at room temperature (23° C.). Polyhedra yields were enumerated by taking images of polyhedra and counted using the OpenCFU program. Due to the size differences of polyhedra from the various viral infections, the purified polyhedra from each infection were solubilized in 0.1 M Na$_2$CO$_3$ (pH 10.5). Bovine serum albumen (BSA) of known concentration (NEB) was serially diluted with 0.1 M Na$_2$CO$_3$ (pH 10.5). A Bio-Rad protein assay dye reagent concentrate system was used to construct the standard curve and estimate the protein yield of solubilized polyhedra for statistical comparison.

To support polh expression differences between AcBac-Polh and AcBac-M2-Polh in HF cells, the green fluorescent protein (GFP) gene was used for the comparison. The 1GFP gene was retrieved from pBlueGFP by double digestion of BamHI/XhoI and cloned 1 between the BamHI and XhoI sites of pFastBac-M2 to generate pAcBac-M2-GFP (FIG. 2). Ultimately, AcBac-M2-GFP virus was generated in HF cells using the Bac-To-Bac system following procedures recommended by Invitrogen. To compare GFP expression yields between the two vectors, AcBacGFP from Cheng et al. and AcBac-M2-GFP were used to infect HF cells in triplicate as described above (FIG. 2) (Cheng et al., 2013). At day 4 P.I., GFP expression yields from HF cells infected with the two viruses were estimated using a FilterMax F5 Multi-Mode Microplate Reader (Molecular Devices, Sunnyvale, 19 CA). GFP expression differences were analyzed using Excel (Microsoft).

In addition to the use of polyhedrin and GFP for protein expression comparison between different donor plasmid vectors, an HPV16 major capsid protein L1 was used to quantify protein expression levels of the donor vectors developed in this project. The L1 gene was amplified using a pair of primers (HPV16 L1-F1-XbaI and HPV16 L1-R1-HindIII; Table 1) with plasmid pML2D, which contains a copy of HPV16 L1, as the template in PCR. The PCR product was cloned into the pGEM-T Easy vector (Promega) and confirmed by sequencing. The L1 gene was retrieved by digestion with XbaI and HindIII (NEB) and ligated into the XbaI/HindIII sites of pFastBac™1 and pFastBac-M2 to produce pAcBac1-L1 and pAcBac-M2-L1, respectively, for transformation of DH10Bac cells (FIG. 2). The resulting recombinant bacmid AcBac-L1 and AcBac-M2-L1 DNAs were transfected into HF cells as described above and BV was harvested for subsequent infection. HF cells in 6-well plates were infected in triplicate with various viruses constructed for L1 expression at an MOI of 1. HF cells infected with AcBacGFP lacking L1 were used as a negative control. At 72 h P.I., cells were harvested and lysed in a radioimmunoprecipitation assay buffer (RIPA; 25 mM Tris-HCl pH 7.6, 150 mM NaCl, 1% NP-40, 1% sodium deoxycholate, 0.1% SDS) and sonicated for SDS-PAGE. Equal amounts of proteins in the lysates (100 μg) were loaded on two identical acrylamide gels for protein separation. Proteins on the gel were then transferred to nitrocellulose membranes. One blot was probed with a mouse anti-HPV16 L1 monoclonal antibody (BD Pharmingen, San Jose, Calif.) for L1 expression yield comparison and the other blot was probed with a *Naegleria gruberi* alpha-tubulin monoclonal antibody (Developmental Studies Hybridoma Bank, University of Iowa) for protein loading normalization. A goat anti-mouse horseradish peroxidase (HRP) conjugated secondary antibody (Bio-Rad) was used to bind to the primary antibodies (L1 and tubulin) for color development. The blots were photographed, the L1 and tubulin signals were quantified by densitometry using ImageJ, and results were statistically tested using the T-test of Excel (Microsoft).

To understand whether protein expression differences of these vectors are correlated with gene transcription, polh mRNA levels between AcBac-Polh and AcBac-M2-Polh were compared. HF cells were infected separately with AcBac-Polh and AcBac-M2-Polh at an MOI of 5 in triplicate (FIG. 2). At day 4 P.I., infected cells were harvested and total RNA extracted using Tri Reagent (Molecular Research Center, Cincinnati, Ohio) following the protocol recommended by the reagent provider. Total RNA (1 μg) from each isolation was digested with RQ1 RNase-Free DNase (Promega) to remove DNA contamination following the protocol recommended by the enzyme provider. The DNA-free RNA was used for cDNA synthesis using primers oligo dT and 28S-R with a DyNAmo cDNA synthesis kit (NEB). cDNA was used as the template in polh mRNA level comparison between AcBac-Polh and AcBac-M2-Polh normalized to the housekeeping 28S gene. The 28S-F and 28S-R primer pair was used for 28S and AcpolhF and AcpolhR1 primer pair for polh in separate reactions in the same run for real-time qPCR analysis using a Bio-Rad iCycler iQ system according to Xue and Cheng with the modification only at the annealing temperature that was changed to 64.5° C. (Xue and Cheng, 2010). The inverse of the threshold cycle (Ct) between polh mRNA levels of AcBac-Polh and AcBac-M2-Polh relative to 28S Ct was statistically analyzed by the T-test of Excel (Microsoft).

As can be seen from the results presented herein, since the pFastBac-M2 and pFastBac-Dual-M2 vectors have the same MCS as the parental commercial pFastBac™1 and pFastBac™ Dual vectors, researchers who are using these vectors for protein expression can simply transfer these genes into the improved pFastBac-M2 and pFastBac-Dual-M2 to test for higher protein expression yields to reduce protein production costs. All other baculovirus vectors using the 50 bp polh promoter and SV40 pA can be modified to include the cis element and to replace SV40 pA with the polh pA fragment for improved protein expression yields in HF cells.

The general inventive concepts have been described above both generically and with regard to specific embodiments. Although the invention has been set forth in what is believed to be some preferred embodiments, a wide variety of alternatives known to those of skill in the art can be selected within the broader disclosure. The invention is not otherwise limited, except for the recitation of the claims set forth below.

What is claimed is:

1. A method of improving protein expression in a cell capable of being infected by AcMNPV comprising:
   (i) providing a first AcMNPV sequence that has been modified to comprise a heterologous nucleic acid encoding a cis element having 95% to 100% identity to SEQ ID NO:1, a polh promoter, a polh ORF, and a polh pA signal sequence; wherein the cis element is located 147 bp upstream of the polh promoter to form a first modified AcMNPV bacmid, and
   (ii) infecting the cell with the first modified AcMNPV bacmid, wherein the cell infected with the first modified AcMNPV bacmid expresses at least 3 times the level of polyhedrin protein as compared to a cell infected with a second AcMNPV bacmid comprising a SV40 pA signal sequence.

2. A method of improving protein expression in a cell capable of being infected by AcMNPV comprising:
   (i) modifying a first AcMNPV sequence to replace a SV40 pA signal sequence with an AcMNPV polh pA signal sequence to form a first modified AcMNPV bacmid, and
   (ii) infecting the cell with the first modified AcMNPV bacmid, wherein the cell infected with the first modified AcMNPV bacmid expresses increased levels of polyhedrin protein as compared to a cell infected with a second AcMNPV bacmid that still comprises the SV40 pA signal sequence.

3. The method of claim 1, wherein the first modified AcMNPV bacmid expresses 3 times to 4.7 times the level of polyhedrin protein as compared to the level expressed by the cell infected with a second AcMNPV bacmid.

4. The method of claim 1, wherein the first modified AcMNPV bacmid expresses from 3 times to 4 times the level of polyhedrin protein as compared to the level expressed by the cell infected with a second AcMNPV bacmid.

* * * * *

```
                         SEQUENCE LISTING

<160> NUMBER OF SEQ ID NOS: 20

<210> SEQ ID NO 1
<211> LENGTH: 98
<212> TYPE: DNA
<213> ORGANISM: Autographa californica nucleopolyhedrovirus

<400> SEQUENCE: 1
actagagcat agtacgcagc ttcttctagt tcaattacac cattmtagca gcaccggatt      60
aacataactt tccaaaatgt tgtacgaacc gttaaaca                              98

<210> SEQ ID NO 2
<211> LENGTH: 134
<212> TYPE: DNA
<213> ORGANISM: Autographa californica nucleopolyhedrovirus

<400> SEQUENCE: 2
aaggttcgac gtcgttcaaa atattatgcg cttttgtatt tctttcatca ctgtcgttag      60
tgtacaattg actcgacgta aacacgttaa ataaagctag gacatattta acatcgggcg    120
tgttactcga ctag                                                      134

<210> SEQ ID NO 3
<211> LENGTH: 26
<212> TYPE: DNA
<213> ORGANISM: Artificial Sequence
<220> FEATURE:
<223> OTHER INFORMATION: AcPolh-F-XbaI

<400> SEQUENCE: 3
tctagagcat agtacgcagc ttcttc                                          26

<210> SEQ ID NO 4
<211> LENGTH: 25
<212> TYPE: DNA
<213> ORGANISM: Artificial Sequence
<220> FEATURE:
<223> OTHER INFORMATION: AcPolh-R-XhoI

<400> SEQUENCE: 4
ctcgagtaac acgcccgatg ttaaa                                           25

<210> SEQ ID NO 5
<211> LENGTH: 25
<212> TYPE: DNA
<213> ORGANISM: Artificial Sequence
<220> FEATURE:
```

<223> OTHER INFORMATION: AcPolh-F-EcoRI

<400> SEQUENCE: 5
gaattcatgc cggattattc atacc                                    25

<210> SEQ ID NO 6
<211> LENGTH: 36
<212> TYPE: DNA
<213> ORGANISM: Artificial Sequence
<220> FEATURE:
<223> OTHER INFORMATION: Hind-F

<400> SEQUENCE: 6
ataaagctag gacatattta acatcgggcg tgttag                        36

<210> SEQ ID NO 7
<211> LENGTH: 36
<212> TYPE: DNA
<213> ORGANISM: Artificial Sequence
<220> FEATURE:
<223> OTHER INFORMATION: Hind-R

<400> SEQUENCE: 7
atgtcctagc tttatttaac gtgtttacgt cgagtc                        36

<210> SEQ ID NO 8
<211> LENGTH: 27
<212> TYPE: DNA
<213> ORGANISM: Artificial Sequence
<220> FEATURE:
<223> OTHER INFORMATION: Polh-F1-HindIII

<400> SEQUENCE: 8
cccaagcttc ttgtagcagc aatctag                                  27

<210> SEQ ID NO 9
<211> LENGTH: 38
<212> TYPE: DNA
<213> ORGANISM: Artificial Sequence
<220> FEATURE:
<223> OTHER INFORMATION: Polh-R-BamH1

<400> SEQUENCE: 9
cggatccaat atttataggt tttttttatta caaaactg                     38

<210> SEQ ID NO 10
<211> LENGTH: 16
<212> TYPE: DNA
<213> ORGANISM: Artificial Sequence
<220> FEATURE:
<223> OTHER INFORMATION: Promoter-R1

<400> SEQUENCE: 10
gttaatccgg tgctgc                                              16

<210> SEQ ID NO 11
<211> LENGTH: 17
<212> TYPE: DNA
<213> ORGANISM: Artificial Sequence
<220> FEATURE:
<223> OTHER INFORMATION: Promoter-R2

<400> SEQUENCE: 11 aaagggagg tgaactg                                              17

```
<210> SEQ ID NO 12
<211> LENGTH: 18
<212> TYPE: DNA
<213> ORGANISM: Artificial Sequence
<220> FEATURE:
<223> OTHER INFORMATION: Promoter-R3

<400> SEQUENCE: 12
gtctcattac aatggctg                                                       18

<210> SEQ ID NO 13
<211> LENGTH: 24
<212> TYPE: DNA
<213> ORGANISM: Artificial Sequence
<220> FEATURE:
<223> OTHER INFORMATION: Promoter-R4

<400> SEQUENCE: 13
ctatatattg atagacattt ccag                                                24

<210> SEQ ID NO 14
<211> LENGTH: 24
<212> TYPE: DNA
<213> ORGANISM: Artificial Sequence
<220> FEATURE:
<223> OTHER INFORMATION: Promoter-F

<400> SEQUENCE: 14
gatatcatgg agataattaa aatg                                                24

<210> SEQ ID NO 15
<211> LENGTH: 22
<212> TYPE: DNA
<213> ORGANISM: Artificial Sequence
<220> FEATURE:
<223> OTHER INFORMATION: CisF1

<400> SEQUENCE: 15
gtagcatagt acgcagcttc tt                                                  22

<210> SEQ ID NO 16
<211> LENGTH: 40
<212> TYPE: DNA
<213> ORGANISM: Artificial Sequence
<220> FEATURE:
<223> OTHER INFORMATION: Polh-R-BamH1

<400> SEQUENCE: 16
cccggatcca atatttatag gtttttttat tacaaaactg                               40

<210> SEQ ID NO 17
<211> LENGTH: 25
<212> TYPE: DNA
<213> ORGANISM: Artificial Sequence
<220> FEATURE:
<223> OTHER INFORMATION: Ac-Polh-F-EcoRI

<400> SEQUENCE: 17
gaattcatgc cggattattc atacc                                               25

<210> SEQ ID NO 18
<211> LENGTH: 23
<212> TYPE: DNA
<213> ORGANISM: Artificial Sequence
<220> FEATURE:
<223> OTHER INFORMATION: Ac-Polh-R-XbaI
```

```
<400> SEQUENCE: 18
tctagattaa tacgccggac cag                                          23

<210> SEQ ID NO 19
<211> LENGTH: 30
<212> TYPE: DNA
<213> ORGANISM: Artificial Sequence
<220> FEATURE:
<223> OTHER INFORMATION: HPV16 L1-F1-XbaI

<400> SEQUENCE: 19
tctagaatgg aggtgacttt tatttacatc                                   30

<210> SEQ ID NO 20
<211> LENGTH: 27
<212> TYPE: DNA
<213> ORGANISM: Artificial Sequence
<220> FEATURE:
<223> OTHER INFORMATION: HPV16 L1-R1-HindIII

<400> SEQUENCE: 20
aagcttttac agcttacgtt ttttgcg                                      27
```